United States Patent [19]

Bird

[11] 4,127,123
[45] Nov. 28, 1978

[54] VENTILATOR AND METHOD

[75] Inventor: Forrest M. Bird, Palm Springs, Calif.

[73] Assignee: Minnesota Mining and Manufacturing Company, St. Paul, Minn.

[21] Appl. No.: 730,725

[22] Filed: Oct. 8, 1976

Related U.S. Application Data

[63] Continuation-in-part of Ser. No. 593,667, Jul. 7, 1975, Pat. No. 4,044,763.

[51] Int. Cl.$^2$ ............................................. A61M 16/00
[52] U.S. Cl. ............................ 128/145.8; 137/624.14
[58] Field of Search ............... 128/145.8, 145.6, 145.5, 128/DIG. 17, 188; 137/624.14

[56] References Cited

U.S. PATENT DOCUMENTS

| | | | |
|---|---|---|---|
| 3,362,404 | 1/1968 | Beasley | 128/145.8 |
| 3,434,471 | 3/1969 | Liston | 128/145.8 |
| 4,007,736 | 2/1977 | Schreiber | 128/145.8 |

Primary Examiner—Henry J. Recla
Attorney, Agent, or Firm—Cruzan Alexander; Donald M. Sell

[57] ABSTRACT

Ventilator having an inhalation phase and an exhalation phase in its operative cycle for use with a source of gas under pressure. A master sequencing cartridge having an inlet adapted to be connected to a source of gas under pressure and an outlet is provided. The cartridge has a valve member movable between open and closed positions to control the flow of gas from the inlet to the outlet. The cartridge is provided with a diaphragm capable of operating under differentials in pressure for causing movement of said valve member. A breathing circuit outlet is provided and is coupled to the outlet of the master sequencing cartridge. A pneumatic control circuit is provided for controlling the movement of the valve member of the master sequencing cartridge between open and closed positions and includes a volume/rate control valve assembly having an inlet and an outlet. The inlet of the control valve assembly is coupled to the outlet of the master sequencing cartridge and the inlet is coupled to the diaphragm means of the cartridge whereby the timing for moving the valve member between open and closed positions is determined by the rate of flow of gases through the volume/rate control valve assembly. A demand base line compensator is coupled to the breathing circuit outlet and provides demand constant positive airway pressure.

7 Claims, 8 Drawing Figures

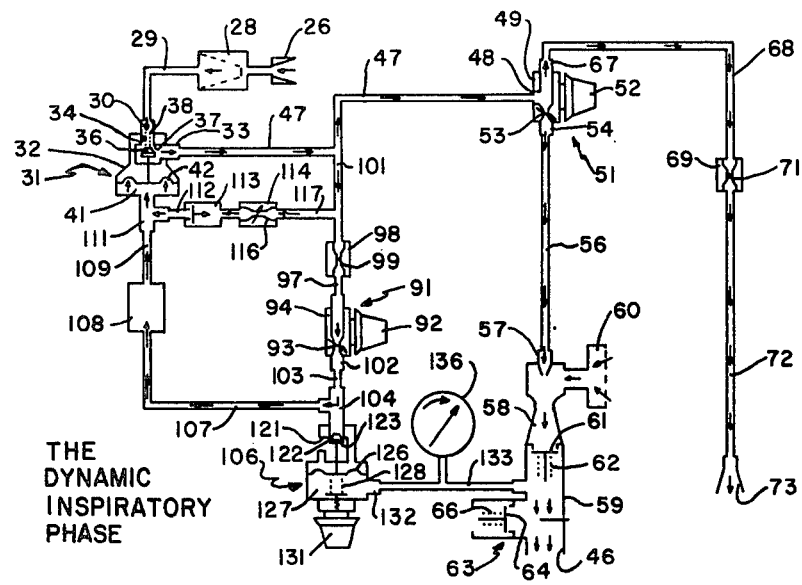
FIG.—3
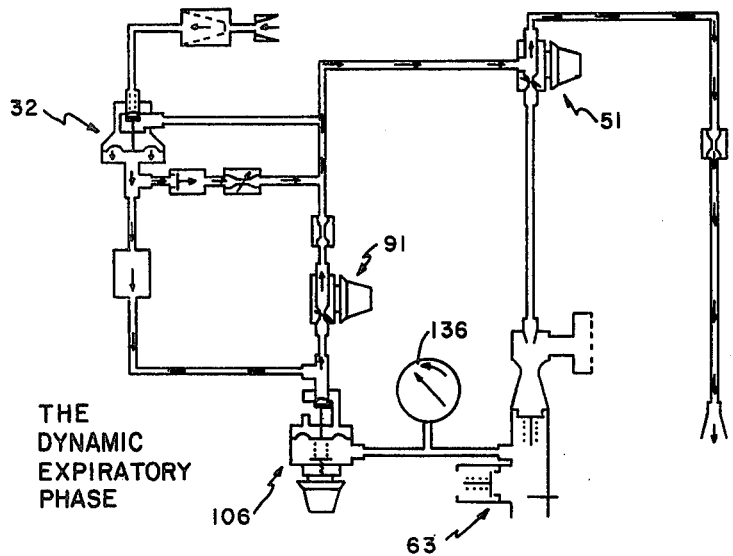
FIG.—4
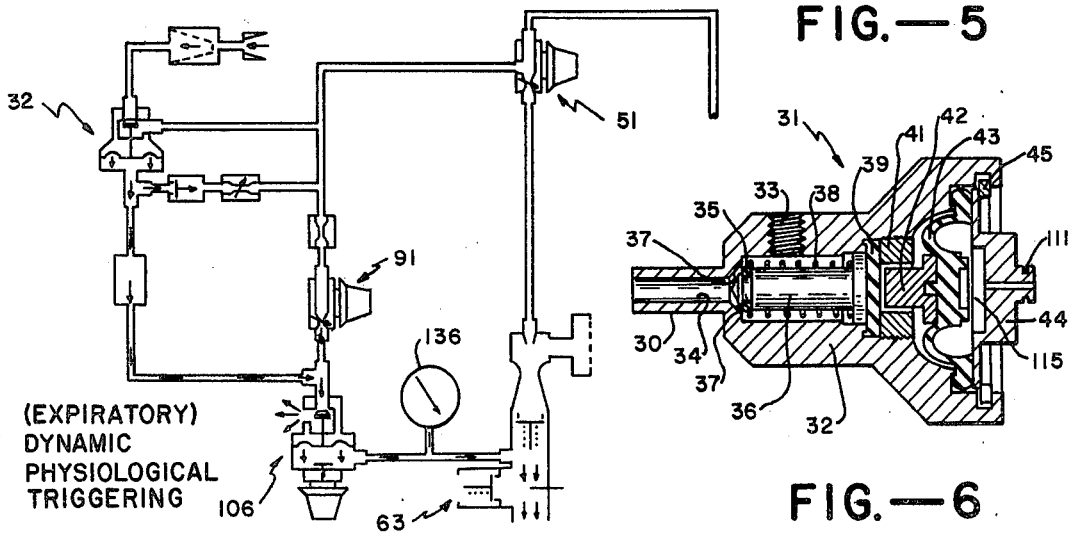
FIG.—5
FIG.—6

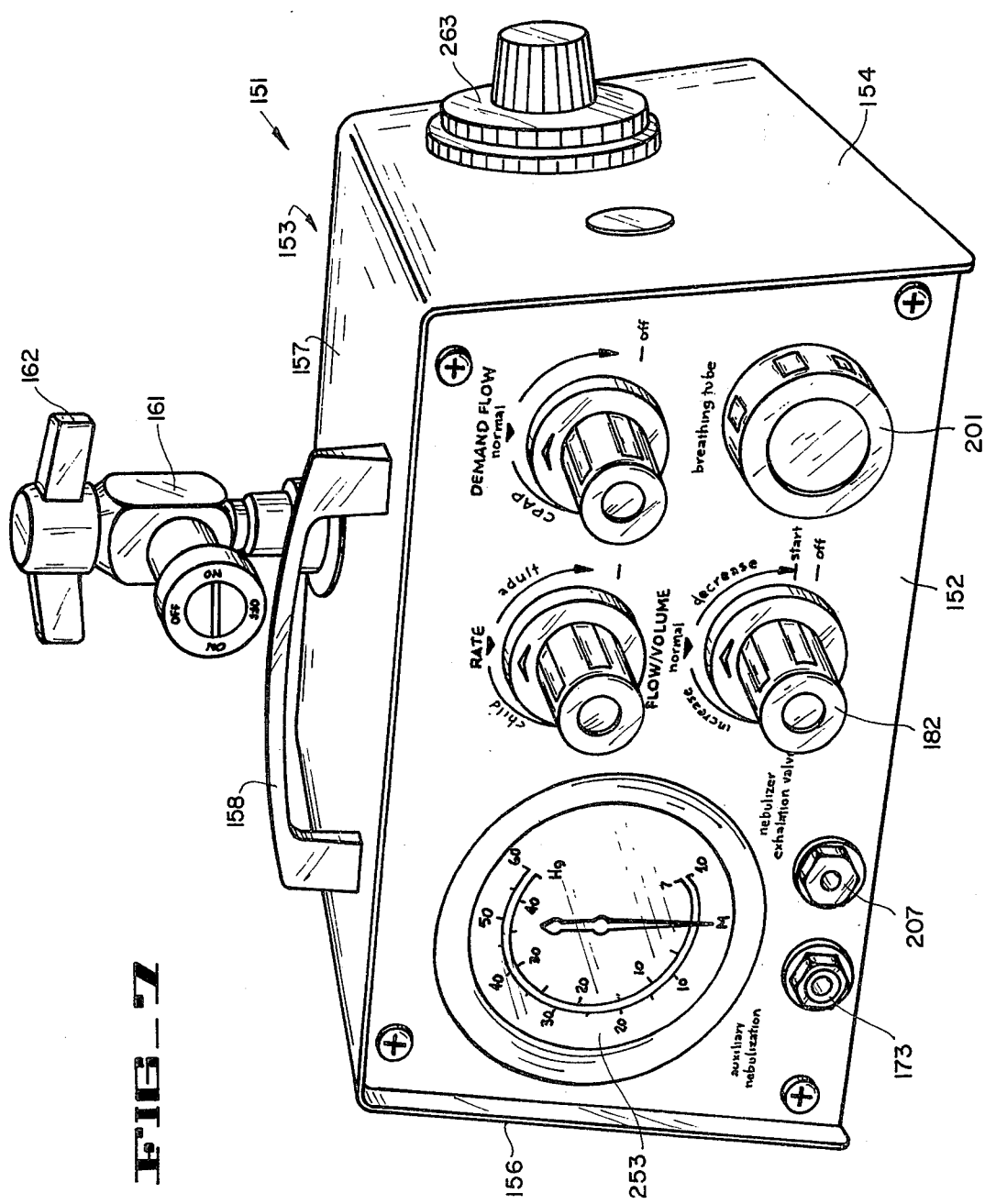

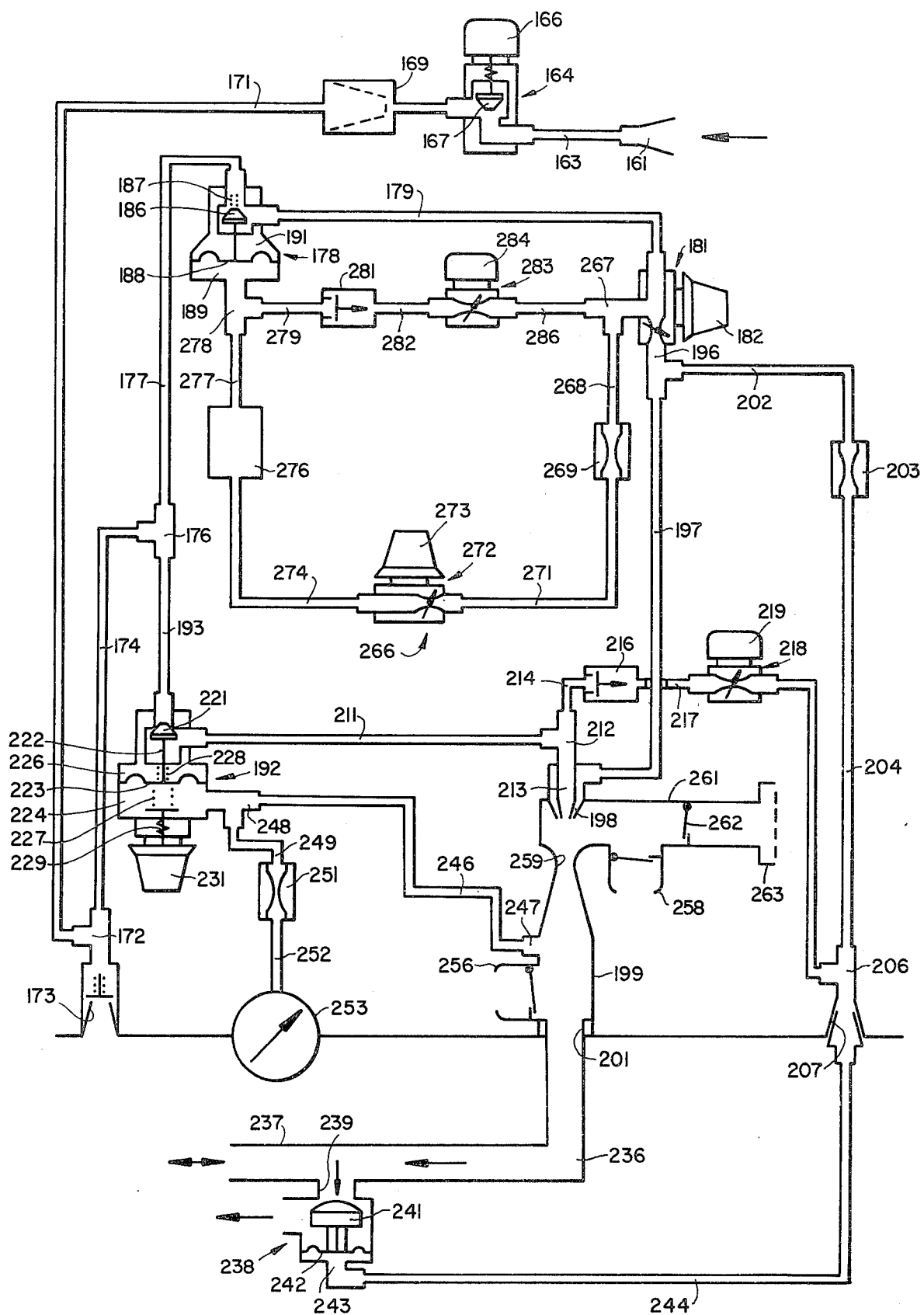
FIG_8

VENTILATOR AND METHOD

RELATED APPLICATION

This application is a continuation in part of application Ser. No. 593,667 filed on July 7, 1975 now U.S. Pat. No. 4,044,763.

BACKGROUND OF THE INVENTION

Emergency medicine has emerged as a major specialty during recent years and involves initial management at the site of physiological failure or trauma, the transport to a formal medical facility and emergency room care. In connection with such emergency medicine, there has arisen a need to provide ventilatory care. Because of the complexities created by patients sized from a small infant to a large adult with their vast differences in pulmonary tidal volumes and the rates desired, it has been very difficult to provide a satisfactory ventilator which can meet these problems and at the same time be simple enough to operate so that it can be utilized by medical transport crews, paramedics and the like without unduly compromising the requirement of the patient being cared for. There is, therefore, a need for a ventilator which can meet these requirements.

SUMMARY AND OBJECTS OF THE INVENTION

The ventilator has an inhalation phase and an exhalation phase in its operative cycle and is for use with a source of gas under pressure. A master sequencing cartridge is provided having an inlet adapted to be connected to the source of gas under pressure and an outlet. It has a valve member movable between open and closed positions to control the flow of gas from the inlet to the outlet. Diaphragm means is coupled to the valve member for moving the same between open and closed positions. The ventilator is provided with a breathing circuit outlet and means is provided coupling the breathing circuit outlet to the outlet of the master sequencing cartridge. Means is provided for controlling the movement of the valve member between open and closed positions of the master sequencing cartridge and includes a volume/rate control valve assembly having an inlet and an outlet. Means is provided for coupling the inlet of the control valve assembly to the outlet of the master sequencing cartridge. Means is also provided for connecting the inlet to the diaphragm so that gas under pressure can be supplied to the diaphragm to move the valve member between said open and closed positions. When desired, a balance reservoir is provided for controlling the flow from the volume/rate control valve assembly to the diaphragm to smoothe the operation of the master sequencing cartridge.

In general, it is an object of the present invention to provide a ventilator and method in which a single control can be utilized to provide control capabilities ranging over a very wide range.

Another object of the invention is to provide a ventilator of the above character which is capable of being used for human beings of all ages.

Another object of the invention is to provide a ventilator and method of the above character which is particularly useful in emergency medicine.

Another object of the invention is to provide a ventilator and method of the above character in which additional gas under pressure is supplied to the patient upon demand of the patient.

Another object of the invention is to provide a ventilator and method of the above character in which time cycling is utilized.

Another object of the invention is to provide a ventilator and method of the above character in which a constant positive airway pressure can be provided.

Another object of the invention is to provide a ventilator and a method of the above character in which elevated base lines utilized in the constant positive airway pressure are controlled by the use of the exhalation valve.

Another object of the invention is to provide a ventilator and method of the above character in which overpressure relief valve means is provided at the master venturi assembly.

Additional objects and feature of the present invention will appear from the following description in which the preferred embodiment is set forth in detail in conjunction with the accompanying drawing.

BRIEF DESCRIPTION OF THE DRAWINGS

FIG. 3 is a schematic diagram of the various components of the ventilator shown in FIG. 2 and showing the flow of gases during the dynamic inspiratory phase.

FIG. 4 is a schematic diagram similar to FIG. 3 but showing the flow of gases during the dynamic expiratory phase.

FIG. 5 is a schematic diagram similar to FIGS. 3 and 4 showing the flow of gases during dynamic physiological triggering.

FIG. 6 is a cross-sectional view of the normally open master sequencing cartridge shown in FIGS. 3, 4 and 5.

FIG. 7 is a front elevational view of another embodiment of a ventilator incorporating the present invention.

FIG. 8 is a schematic diagram of the various components of ventilators shown in FIG. 7 and showing the interconnections between the same.

DESCRIPTION OF PREFERRED EMBODIMENT

Figure 1:
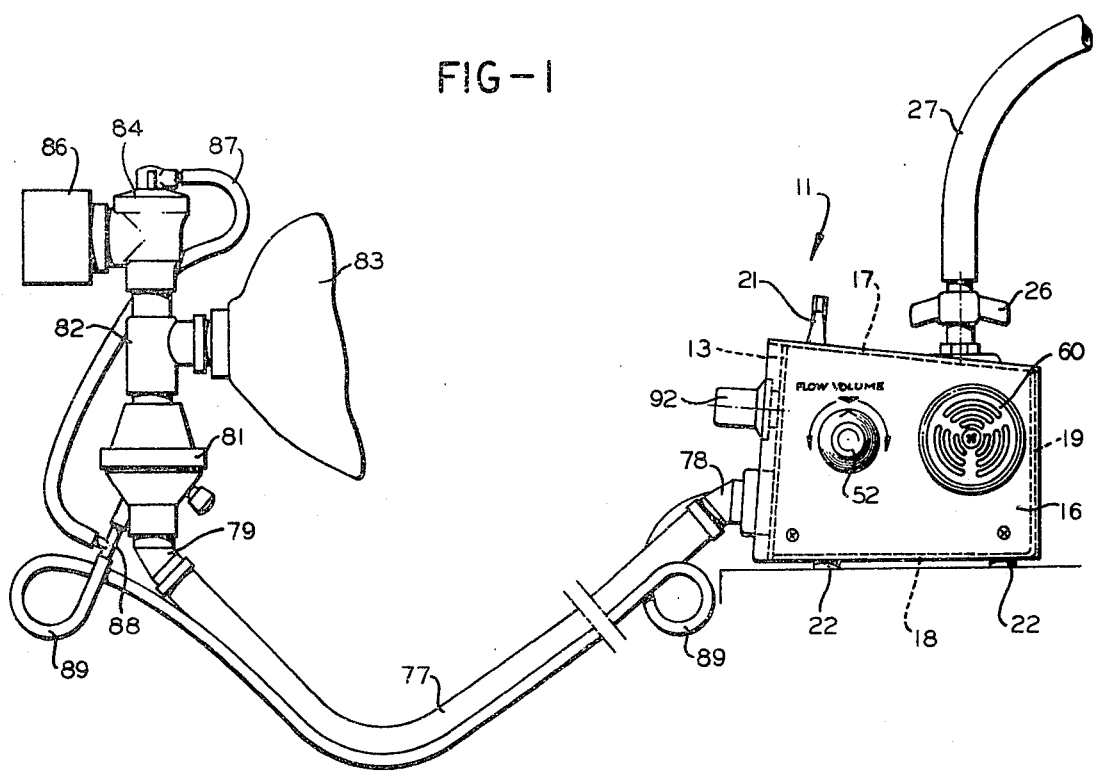
FIG. 1 is a front elevational view of a ventilator incorporating the present invention.
Figure 2:
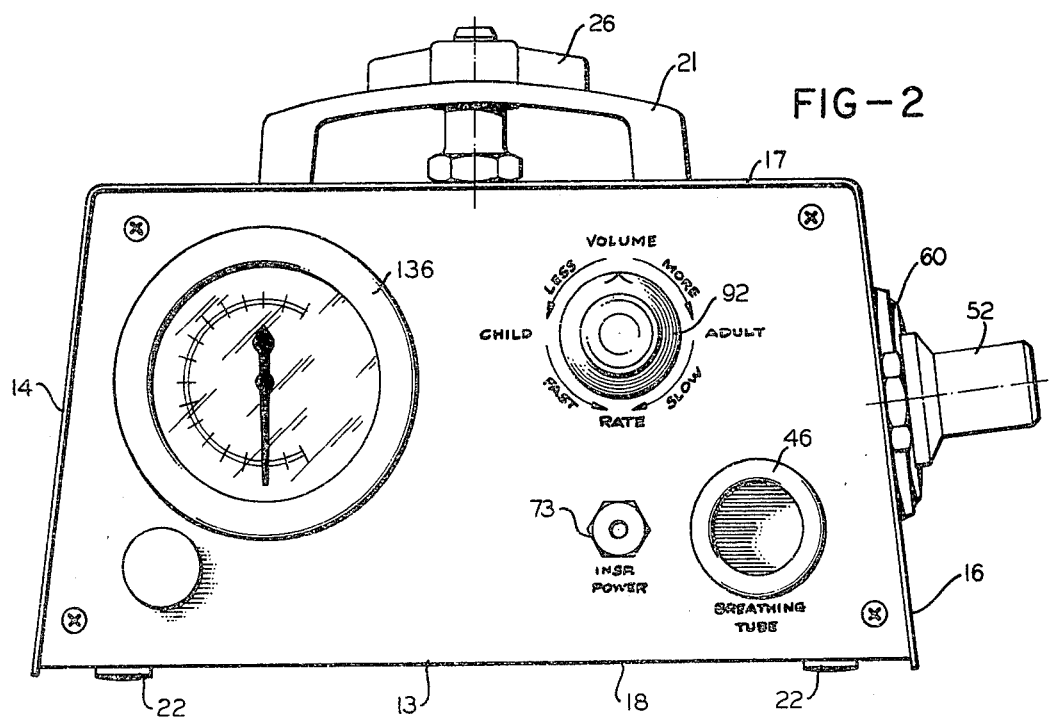
FIG. 2 is an enlarged front elevational view of the ventilator without the breathing tube and other accessories attached thereto.

The ventilator 11 shown in the drawings consists of a case 12 which has the configuration shown and which is provided with a front wall 13, inclined side walls 14 and 16, top and bottom walls 17 and 18, and a rear wall 19. A handle 21 is provided on the top wall to make it possible to readily carry the ventilator from one location to another. It is also provided with rubber feet 22 which are secured to the bottom wall 18.

An inlet fitting 26 is mounted in the top wall 17 and is adapted to be secured to a source of gas under pressure such as provided by the inlet hose 27. The hose 27 can be connected to a source of oxygen or air, or a combination of the same at a suitable pressure as, for example, 50 psi. Gas which is supplied through the inlet fitting 26 passes through an inlet filter 28 provided within the case 12. The outlet of the inlet filter is connected by a tube 29 to the inlet 30 of a master sequencing cartridge 31 having a cartridge body 32. The master sequencing cartridge body 32 is provided with an outlet 33. The cartridge body 32 is also formed with a flow passage 34 which establishes communication between the inlet 30 and the outlet 33. Valve means is provided for interrupting the flow through the flow passage 34 and thereby interrupting the flow from the inlet 30 to the outlet 33 and consists of a poppet valve or valve member 36 carrying an O-ring 35 which is adapted to engage a valve seat 37 (see FIG. 6) to interrupt the flow passage 34.

The poppet valve 36 is slidably mounted in the body 32 for slidable movement between open and closed positions with respect to the valve seat 37. Yieldable means is provided for urging the poppet valve 36 toward an open position and consists of a spring 38 having one end engaging the body and having the other end engaging the flanged poppet valve 36. A disc-like seal 39 which is retained within the body 32 by a retaining ring 41 seals the poppet valve from the remainder of the master sequencing cartridge. The poppet valve 36 is adapted to be moved towards a closed position by a button 42 slidably mounted in the retaining ring 41 and engaging the seal 39 in a region opposite the poppet valve 36. The button 42 is carried by the central portion of a diaphragm 43 retained within the body 36 by an end cap 44 which clamps the outer margin of the diaphragm 43 between the body and the cap. The end cap 44 is held in place by a retaining ring 45.

Means is provided for connecting the outlet of the master sequencing cartridge to a breathing tube outlet 46 which is mounted on the front panel or wall 13. Such means includes a tube 47 which is connected to the outlet 33 of the master sequencing cartridge 32 and is connected to the inlet 48 of a manifold 49 provided as a part of the inspiratory flow/volume control valve assembly 51. The valve assembly 51 is of a conventional type and is mounted in the side wall 16 and has a control knob 52 which is accessible from the outside of the case 12. The control knob 52 controls the adjustment of the orifice 53 in the manifold and supplies gas through an outlet 54 through a tube 56. The tube 56 is connected to the center jet 57 mounted in one end of the master venturi assembly 58. The master venturi assembly 58 is mounted on a breathing circuit manifold which is mounted upon the rear side of the front panel 13 and is connected to the breathing tube receptacle 46. A gate valve 61 is provided within the breathing circuit manifold and yieldable means in the form of a spring 62 is provided for retaining the gate valve 61 in a normally closed position. An over-pressure relief valve assembly 63 is mounted on the breathing circuit manifold 59 adjacent the outlet 46 and is provided with a gate valve 64 which is normally held in a closed position by yieldable means in the form of a spring 66.

The manifold 59 is provided with another outlet 67 which is connected by a tube 68 to one side of a member 69 having a fixed nebulizer orifice 71 therein. The other side of the member 69 is connected to a tube 72 which is connected to an inspiratory service or power socket 73 mounted on the front panel 13.

A conventional patient breathing circuit 76 is connected to the breathing tube receptacle 46 and the inspiratory service socket 73 and, as shown, consists of a large tube 77 which is provided with a fitting 78 which is mounted by a friction fit within the breathing tube receptacle 46. The other end of the tube 77 is connected to a fitting 79 which is mounted in one end of a nebulizer 81 of a conventional type generally described in U.S. Pat. No. 3,172,406. The other end of the nebulizer 81 is connected to one leg of a tee 82. Another leg of the tee 82 has a patient adapter of a suitable type such as a face mask 83 mounted thereon.

An exhalation valve assembly 84 of a conventional type is mounted on the remaining leg of the tee 82. The exhalation valve assembly 84 is provided with a muffler 86. Means is provided for supplying gas under pressure to the exhalation valve to maintain the same closed during the inspiratory phase and includes a tube 87 which is connected to one leg of a tee 88. Another leg of the tee 88 is mounted in the nebulizer orifice of the nebulizer 81. The remaining leg of the tee 88 is connected by a tube 89 to the inspiratory service socket 73.

Means is provided for controlling the cycling of the master sequencing cartridge 32 to control the flow of gases to the breathing circuit 46 and the inspiratory service socket 73 and consists of a volume/rate control valve assembly 91 which is mounted on the front panel 13. It is of a conventional type and is provided with a control knob 92 which is accessible from the front panel for adjusting the flow of gas through an adjustable orifice 93 provided in the manifold 94 forming a part of the control valve assembly 91. The mainfold 94 is provided with an inlet 96 which is connected by a tube 97 to one side of a member 98 having a fixed balance orifice 99 provided therein. The other end of the member 98 is connected by a tube 101 which is connected to tube 47 which is, in turn, connected to the outlet of the master sequencing cartridge 32.

The outlet 102 of the control valve assembly 91 is connected by tube 103 to a tee 104 mounted upon a physiologically triggering servo cartridge 106. The other leg of the tee 104 is connected by a tube 107 which is connected to one end of a balance reservoir 108. The other end of the balance reservoir 108 is connected by tube 109 to tee 110 mounted in the servo port 111 of the master sequencing cartridge 31 and in communication with a chamber 115 provided on one side of the diaphragm 43. The other leg of the tee 111 is connected by tube 112 to a one-way check valve assembly 113 which serves as an inspiratory/expiratory ratio check valve. The check valve assembly 113 is connected to a ratio calibration valve assembly 114 which is provided with an adjustable orifice 116. The valve assembly 114 is connected by tube 117 to the tube 101.

A filter 60 of a conventional type is provided which is connected to the master venturi 58 to supply atmospheric air to the master venturi so that it can be mixed with the gases being supplied through the jet 57. The filter 60 is mounted in the side wall 16 of the case 12.

The triggering servo assembly 106 is provided with means for dumping the terminal timing circuit which includes the tube 107 to ambient. Thus, the triggering servo is provided with a flow passage 121 which is open to ambient. The servo assembly 106 is provided with a valve member 122 movable between open and closed positions with respect to a valve seat 123 for interrupting communication between ambient and the tee 104. The valve member is provided with a valve stem 124 for guiding the same. The valve stem is connected to a diaphragm 126. The cartridge 106 is provided with means forming a chamber 127 on one side of the diaphragm so that when the chamber 127 is filled with gas, the diaphragm urges the valve member 122 towards a closed position. Means is provided for yieldably urging the valve member 122 into a normally closed position and includes a spring 128 which engages one side of the diaphragm 126. The other end of the spring is adapted to be engaged by an adjustable member 129 which can be adjusted in position by a control knob 131. The cartridge 106 is provided with a fitting 132 which is in communication with the chamber 127 and which is connected by tube 133 to the breathing circuit manifold 59. The tube 133 is connected by another tube 134 to a manometer 136 which is mounted on the front panel 13 to give an indication of the pressure in the tube 133.

Operation and use of the ventilator in performance of the method for use therewith may now be briefly described as follows. Let it be assumed that the ventilator 11 has been connected to a source of gas under pressure through the tube 27. As soon as source gas is supplied, the source gas is supplied through the fitting 26 through the filter 28 to the inlet of the normally open pneumatically servoed master sequencing cartridge 32. Gas will thus flow from the inlet 31 to the outlet 33 of the cartridge through the tube 47 to the manifold 49 of the inspiratory flow/volume control assembly 51. In addition, gas will be supplied through the tube 101 and the tube 117 to the outlet of the inspiratory/expiratory ratio calibration valve assembly 114 and to the inlet of the manifold 94 of the volume/rate control valve assembly 91 through the balance orifice 99. Gas flow which is metered through the volume/rate control valve assembly 91 is directed into the tee 104 and the inlet of the physiologically triggering servo assembly 106. Flow also passes through the tube 107 through the balance reservoir 108 to the chamber 41 of the normally open master sequencing cartridge 32.

During the dynamic inspiratory phase shown in FIG. 3, gas supplied to the inspiratory flow/volume control valve assembly 51 is supplied through the tube 68, through the fixed nebulizer orifice 71 to the inspiratory service socket 73, through the tube 89 to the tee 88 where gas is supplied to the nebulizer orifice for the nebulizer 81. The gas under pressure is also supplied to the exhalation valve assembly 87 to maintain the exhalation valve assembly in a closed position. The fixed nebulizer orifice 71 controls the rate of nebulization from the nebulizer. There is also gas flow from the manifold 49 through the outlet 54 through the tube 56 to the fixed orifice jet 57 of the master venturi assembly 58. Since the orifice in the master venturi 58 is fixed, the amount of gas passing through the master venturi is adjusted by controlling the rate of flow through the jet 57 by adjustment of the flow through the same by adjustment of the knob 52 and the orifice 53 controlled thereby. The gases passing from the jet 57 will cause additional ambient air to be entrained through the filter 60 and to be delivered through the master venturi assembly 58 to open the gate valve 61 and to deliver the same to the breathing tube receptacle 46. The gases from the breathing tube receptacle are then supplied through the large tube 77 through the main flow passage of the nebulizer 81, through the tee 82 and to the patient adapter in the form of a mask 83 where it is supplied to the patient during the inspiratory phase.

The length of the inspiratory phase is a function of the rate at which the volume/rate control metering valve assembly 91 allows gas flow into the terminal timing circuit which is connected to the tube 107 and which includes the balance reservoir 108 and the chamber 41 behind the diaphragm 39. By metering gas into the chamber 41 at a controlled rate, the pressure rise can be adjustably controlled. Thus, it can be seen that the more limited the flow through the adjustable volume/rate control valve assembly 91, the greater the time required to build up a servoing pressure behind the master sequencing diaphragm 39. The normally open master sequencing cartridge will be pneumatically closed when the servoing pressure against the diaphragm 43 exceeds the opening forces of the spring 38 combined with the piston effect of the inlet gases against the diaphragm seal 39.

The balance orifice 98 spreads the calibration of the volume/rate control valve assembly 91 over 320° of travel of the knob 92. The rate of flow into the terminal timing circuit is determined by the volume/rate control valve assembly 91. During the inspiratory phase, the inspiratory/expiratory ratio check valve assembly 113 is held competent by inspiratory gases back flowing against the inspiratory/expiratory calibration valve 114 to exert pressure against the outlet of the inspiratory/expiratory ratio check valve assembly 113.

The volume/rate control valve assembly 113 is stopped by cams (not shown) to provide minimum and maximum inspiratory time. It can be appreciated that if the valve assembly 91 were completely closed, an infinite inspiratory phase would be held which would be undesirable. The balance reservoir, although not essential, provides additional volume in the terminal timing circuit and permits the use of a less critical volume/rate metering valve assembly 91 for a wide range of functional ventilatory rates. In addition, since it provides a greater volume, there is a more gradual increase in pressure and a tapered effect in the closing of the master sequencing cartridge 31.

The flow of gases during the dynamic inspiratory phase is shown by the arrows in FIG. 3. The flow of gases during the dynamic expiratory phase is shown by arrows in FIG. 4 and the expiratory phase is initiated at the instant of closure of he normally open master sequencing cartridge 32. Closing of the master sequencing cartridge 32 interrupts the flow of gas from the source into the line 47. The remaining pressure of gases supplied to the manifold 49 rapidly decreases by bleeding off through the nebulizer orifice 71 and through the inspiratory service socket 73 and also through the adjustable orifice 53 through the jet 57 and into the breathing circuit 46. This pressure drop in the servoing circuit connected to the line 47 produces a reverse flow of gas from the timing circuit and from the line 107 through the restricted orifice 93 through the balance orifice 99 and into the line or tube 47.

During the expiratory phase, timing gases from the terminal timing circuit connected to the tube 107 are exiled by parallel routes. One route is through the adjustable metering orifice 93 of the volume/rate control valve assembly 91 and through the balance orifice 91 to the line 47. The other route is through the I/E check valve assembly 113 through the I/E ratio calibration valve assembly 114 through the tube 117, the tube 107, to the tube 47 where it is bled off through the breathing tube receptacle 46 and the inspiratory service socket 73.

Back flow through the volume/rate metering valve assembly 91 progressively reduces servoing pressures behind the diaphragm 39 of the master sequencing cartridge. This continues until the pressure in the chamber 41 drops to a suitable value as, for example, 7 to 8 psi in which the opening forces exceed the closing forces and the master sequencing cartridge 32 opens. As soon as the master sequencing cartridge opens, this mechanically starts the next dynamic inspiratory phase.

As can be seen, there is a differential between the opening and closing pressures of the master sequencing cartridge 32. The opening forces are due to a combination of the force applied by the spring 38 and the force which is applied by the pressure of the inlet gases against the seal 39.

The purpose of the parallel route for the exiled gases from the terminal timing circuit is to allow calibration of the inspiratory/expiratory ratios. The normal inspiratory/expiratory ratio of the timing circuit is established at approximately 1 to 15 but to allow the clinical option of ratios less than 1 to 3, or even greater than 1 to 3. The inspiratory/expiratory ratio check valve assembly 113 and inspiratory/expiratory ratio calibration valve assembly 114 serve as an expiratory bypass circuit. The basic expiratory time as referenced to inspiratory time is reduced by increasing the rate of expiratory outflow from the terminal timing circuit by progressively increasing the size of the orifice of the inspiratory/expiratory calibration valve assembly 114. Thus, while the basic inspiratory/expiratory ratio is established by the differential in opening pressure of the master sequencing cartridge 32 and the rate of inspiratory and expiratory flow across the volume/rate control metering valve, the inspiratory/expiratory ratio is calibrated by increasing the rate of flow from the expiratory circuit by the expiratory bypass loop.

Upon initiation of the expiratory phase, gas under pressure is no longer supplied to the inspiratory service socket 73 and permits the exhalation valve assembly 84 to open and to permit the patient to exhale to the atmosphere.

During the mechanical inspiratory phase and prior to the expiration of the expiratory timing period, the patient can trigger the ventilator into a mechanical inspiratory phase as shown in FIG. 5 to provide dynamic physiological triggering during the expiratory phase. This is accomplished by "dumping" the pressure between the volume/rate metering valve assembly 91 and the chamber 41 to the atmosphere during any part of the mechanical expiratory phase. Normally, the piston effect (opening pressure) against the valve member 122 is balanced by the spring 128 providing a closing force. Thus, a precise balance between the opening and closing forces can be adjustably established by adjustment of the knob 131. The large area diaphragm is superimposed between the valve member 122 and the spring 128 with the reference side of the diaphragm 126 being vented to ambient. The servoing side of the chamber 128 of the servo 106 is connected by the tube 133 to the breathing circuit manifold 59. During the positive pressure inspiratory phase, the diaphragm 126 is loaded with inspiratory gases to provide a closing force.

In the event that the patient exerts a breath during the inspiratory phase, a sub-ambient condition is created in the breathing tube receptacle 46 which is conveyed to the chamber 127. This creates an opening force to open the valve member 122 against the force of the spring 128 to vent the line or tube 127 to the atmosphere. By way of example, the spring 128 can be adjusted to permit the servo 106 to move to an open position when the physiological pressure drops between −2 and −3 cm of $H_2O$.

The gases within the terminal timing circuit are normally deadheaded in the tee 104 against the inlet of the physiologically triggered servo valve. Thus, it can be seen that as soon as a pressure drop is created within the breathing circuit during the exhalation phase, the valve member 122 is moved to an open position to dump the terminal timing circuit to the atmosphere to cause the master sequencing cartridge 32 to instantaneously shift to the inspiratory phase.

With the ventilator it can be seen that the mechanical airway pressures are continuously monitored by the manometer 136. Peak pressure limiting is provided by an adjustable spring-loaded pressure relief valve with pressure governor assembly 63. Relieving pressure may reach about 65 cm of $H_2O$. However, if desired, this can adjusted.

From the foregoing, it can be seen that there has been provided a ventilator and method in which a single control can be utilized to determine both the inspiratory and expiratory times and which can be utilized on human beings of all ages. The ventilator is one which is particularly useful in emergency medicine and which can be utilized by relatively unskilled personnel.

With the ventilator it is possible with one control valve to obtain flow rates which are satisfactory ranging from an infant to an adult. It is possible to maintain an almost constant inspiratory/expiratory time ratio from operative cyclic frequencies from over approximately 30 per minute down to approximately 5 per minute and to provide a volume of gas to the patient which is substantially inverse to the rate. In other words, at high frequencies there is a small tidal volume and at low frequencies there is a large tidal volume which meet the requirements for an infant and an adult, respectively.

Another embodiment of the ventilator incorporating the present invention is shown in FIGS. 7 and 8. As shown therein, it consists of a case 151 which includes a front panel 152 and a U-shaped member 153 which forms side walls 154 and 156 and a top wall 157. The top wall 157 has a handle 158 mounted thereon for carrying the ventilator. An inlet fitting 161 which carries a wing nut 162 is provided so that the fitting 161 can be connected to a suitable source of gas under pressure as, for example, a gas having a pressure of 50 p.s.i.

The inlet fitting 161 is connected by a tube 163 to a master on-off switch 164. The master on-off switch 164 is provided with a knob 166 which is adapted to move a valve member 167 between open and closed positions to control the flow of source gas through the on-off switch. The outlet of the on-off switch is connected by a tube 168 to a filter 169. The filter 169 is connected by a tube 171 to a tee 172. The tee 172 is mounted in an auxiliary nebulization socket 173 carried by the front panel 152. The other leg of the tee 172 is connected by a tube 174 to one leg of a tee 176. Another leg of the tee 176 is connected by a tube 177 to the inlet of a master sequencing cartridge 178. The outlet of the master sequencing cartridge 178 is connected by a tube 179 to the inlet of an inspiratory flow/volume control valve assembly 181 which is provided with a control knob 182. The master sequencing cartridge 178 is provided with a valve member movable between open and closed positions for controlling the flow of gas from the inlet to the outlet and which is urged toward a normally open position by a spring 187. The valve member 186 is provided with the valve stem 187 which is carried by a diaphragm 188. First and second chambers 189 and 191 are provided on opposite sides of the diaphragm.

In addition to source gas being supplied to the master sequencing cartridge 178, source gases supplied to a demand base line compensator 192 by having its inlet connected by tube 193 to the other leg of the tee 176. A tee 196 is provided in the outlet of the inspiratory flow/volume control 181. One leg of the tee 196 is connected by a tube 197 to the outer jets 198 of a master venturi assembly 199 which has its outer end mounted in a breathing outlet 201 provided on the front panel 152. The other leg of the tee 196 is connected by tube 202 to a nebulizer orifice 203 and the nebulizer orifice 203 is connected by a tube 204 to one leg of a tee 206 which is mounted in the nebulizer exhalation valve socket 207.

The outlet of the demand base line compensator 192 is connected by a tube 211 to a tee 212 which is mounted in the center jet 213 of the master venturi assembly 199. The other leg of the tee 212 is connected by a tube 214 to a one-way check valve 216. The check valve 216 is connected by a tube 217 to a fail safe base line limiting control valve 218 which is provided with a control knob 219. The outlet of the fail safe base line limiting control knob 219 is connected by a tube 221 to one of the legs of the tee 206 and thus to the nebulizer exhalation socket 207. The demand base line compensator is provided with a valve member 221 which is adapted to be moved between the open and closed positions to control the flow of gas through the demand base line compensator 192. The valve member 221 is provided with a stem 222 which is carried by a diaphragm 223. First and second chambers 224 and 226 are provided on opposite sides of the diaphragm 223. A pair of the springs 227 and 228 are provided on opposite sides of the diaphragm 223. Means are provided for adjusting the pressure applied to the diaphragm 223 by the spring 227 and consists of a screw 229 which can be adjusted by turning a knob 231.

The ventilator is adapted to be connected to a conventional breathing circuit such as that disclosed in conjunction with the foregoing embodiments. Thus, as shown in schematics in FIG. 8, the breathing tube socket 201 can have a large tube 236 mounted therein. This large tube 236 is connected into a patient adapter 237 which is connected into the airway of the patient. An exhalation valve assembly 238 is coupled to the patient adapter 237 and is provided with a flow passage 239 open to ambient which is adapted to be opened and closed by a valve member 241 carried by a diaphragm 242. A chamber 243 is provided on one side of the diaphragm and is connected by a tube 244 to the nebulizer/exhalation valve socket 207.

Means is provided for sensing the pressure in the patient airway and supplying this information pneumatically to the chamber 224 of the demand base line compensator 192 and consists of a tube 246 which is connected to a fitting 247 provided near the outlet end of the master venturi assembly 199 and which is connected to a tee 248 mounted on the demand base line compensator 192 and in communication with the chamber 224. The other leg of the tee 248 is connected by a tube 249 to an orifice 251. The orifice 251 is connected by a tube 252 to a manometer 253 mounted in the front panel 152.

An emergency intake check valve assembly 256 is mounted on the master venturi assembly 199 adjacent the outer end thereof. An overpressure relief valve 258 of a conventional type is mounted on the master venturi assembly 199 in a position which is the head of the throat or venturi-like passage 259 provided in the master venturi assembly 199. A tubular member 261 which carries a proximal gate 262 is mounted on the master venturi assembly 199 and is connected to an inlet filter 263 carried by the sidewall 154 of the case 151.

Means is provided for controlling the entrance of source gas into the chamber 189 of the master sequencing cartridge 178 and for controlling the bleeding off of gas from the same chamber 189. This consists of a loop 266 which includes a tee 267 mounted in the inlet of the inspiratory flow flash volume control valve assembly 181. One leg of the tee is connected by a tube 268 to a balance orifice 269. The balance orifice 269 is connected by a tube 271 into the inlet of a rate control valve assembly 272 provided with an adjustment knob 273. The outlet of the rate control valve assembly 272 is connected by a tube 274 to one end of a balance reservoir 276. The other end of the balance reservoir 276 is connected by a tube 277 to a tee 278. The tee 278 is mounted in the master sequencing cartridge 178 and is in communication with the chamber 189. The other leg of the tee 278 is connected by a tube 279 to a check valve 281. The check valve 281 is connected by a tube 282 to the inlet of an inspiratory/expiratory ratio calibration valve assembly 283 having a control knob 284. The outlet of the valve assembly 283 is connected by a tube 286 to the other leg of the tee 267 to complete the loop.

Operation of the ventilator shown in FIGS. 7 and 8 in performing the present method may now be briefly described as follows. Let it be assumed that the 50 p.s.i. source gas has been connected to the inlet 61. As soon as the master on-off switch 164 is turned on, source gas will be supplied through the line 171 to the inlet side of the master sequencing cartridge 178 and also to the inlet of the demand base line compensator 192. Since the master sequencing cartridge 178 is in the normally open position, gas will be supplied through the line 179 to the inspiratory flow/volume control valve assembly 181 and then through the tube 197 to the outer jets 198 of the master venturi assembly 199 and into the breathing tube 236 to the airway of the patient. At the same time, gas will be supplied from the inspiratory flow/volume control valve assembly 181 through the tube 202, the orifice 203, tube 204, to the nebulizer exhalation valve socket and through the tube 284 to the exhalation valve assembly 238 to move the valve member 241 to close the patient adapter off from ambient so that the air supplied from the master venturi assembly 199 will be delivered to the airway of the patient.

The operation of the control loop 266 which controls the bleeding in of gas into the chamber 189 and the bleeding off of gas from the chamber 189 of the master sequencing cartridge 178 is identical to that hereinbefore described in conjunction with the previous embodiments and thus will not be described in conjunction with the present embodiment. In any event, the master sequencing cartridge 178 will be operated to move the valve member 186 between open and closed positions to control the flow of inlet gas through the tube 179 and to thereby control the inspiratory and expiratory phases of the ventilator. Thus it can be seen that the control loop 266 serves as a timing circuit for the ventilator. Timing still remains a function of the rate control valve assembly 272 with the flow/volume control assembly 181 only affecting the rate when the flow/volume metering orifice becomes smaller than the selected orifice provided by the rate control valve assembly 272. It can be seen that when the flow/volume control valve assembly 181 is adjusted to the closed position, this will cause the ventilator to enter into the expiratory phase. When the master sequencing cartridge 178 moves to a closed position, the chamber 243 and the exhalation valve assembly 238 will be depressurized by its gases being discharged through the tube 204, orifice 203, tube 202, to tube 197 and through the dual jets 198 of the master venturi assembly 199. The rate of opening of the exhalation valve member 241 is controlled by the size of the orifice 203.

Demand constant positive airway pressure (CPAP) for automatic base line control during mechanical or physiological respiration with the ventilator is provided by the demand base line compensator 192. The piston effect of the inlet gases upon the valve member 221 tends to urge the valve member towards an open position. The valve member 221 is balanced by a spring 228 providing an opening force and a spring 227 providing a closing force. An additional closing force is provided by the diaphragm 223 when the chamber 224 is pressurized. The chamber 224 receives its pressure information from the distal end of the master venturi assembly 199 through the tube 246. Opening pressures ranging between 0 and 35 centimeters of water or above are controlled by adjustably compressing the balance spring 227 against the diaphragm 224 so that the valve member 221 is held competent or in a closed position by a combination of forces provided by the balance spring 227 and any positive servoing pressure in the chamber 224 acting upon the diaphragm 223.

By way of example, in illustrating a dynamic function, let it be assumed that the control knob 231 of the base line compensator 192 has been adjusted against the balance spring 227 such that a positive pressure of 10 centimeters of water would be required against the diaphragm 223 to move the valve member 221 to a closed position. This would represent a positive base line of 10 centimeters of water.

As the pressures in the sensing port 247 of the master venturi assembly 199 drop below 10 centimeters of water, the valve member 221 would progressively open delivering source gases from the tube 193 through the tube 211 to the center jet 213 of the master venturi assembly 199. This same gas supplied by the tube 211 is also supplied through the check valve 216 to the adjustable fail safe base line limiting valve to deliver gas to the exhalation valve socket 207 and to the exhalation valve assembly 238 to maintain the exhalation valve member 241 in a closed position. By precisely governing the pressure against the servoing diaphragm 242 carrying exhalation valve 241 the opening pressure of the exhalation valve is most accurately controlled to permit the precise selection of a positive base line within the breathing circuit and against which the patient must breathe during exhalation. The pressure supplied to the servo diaphragm 242 of the exhalation valve carrying the exhalation valve 241 can be precisely controlled. When the fail-safe base line limiting orifice is fixed, the demand base line compensator 192 will increase or decrease pressures against the base line orifice in response to pressure changes in the breathing circuit.

With any selected base line pressure, flow from the demand base line compensator 192 will increase proportionately as pressure decreases in the breathing circuit until the demand base line compensator 192 is fully opened delivering inlet pressure against the center jet 213 of the master venturi assembly and to the inlet of the base line metering valve assembly 218. Under such conditions, as long as physiological demand does not exceed mechanical in-flow into the breathing circuit, downward base line deviation would be governed within pre-established limits by the ventilator.

As pressures in the breathing circuit rise, the diaphragm 223 in the base line compensator 192 proportionately servoes the valve member 221 toward the closed position, decreasing the governed flow of gases to the master venturi assembly 199 and to the base line limiting control valve 218. As flow into the master venturi assembly 199 and into the base line limiting control valve 218 decreases, the governed opening pressure of the exhalation valve proportionately decreases. Flow from the demand base line compensator 192 reaches a minimum regulated value when the preselected base line is reached. When physiological or mechanical flow out of the breathing circuit exceeds the selected base line, flow from the demand base line regulator 192 minimizes and pressure rise within the breathing circuit becomes a factor of resistance to outflow caused by mechanical resistance in the non-competent breathing circuit. As physiological demand starts to decrease breathing circuit pressures below program values, mechanical in-flow is increased with increased exhalation valve gate competency to minimize downward base line deviation. As breathing circuit pressures rise, the competency of the exhalation valve decreases proportionately, minimizing overshoot by automatically decreasing expiratory resistance to outflow from the breathing circuit. It has been noted that there is a lack of any chatter in movement of the exhalation valve 241 in the range of outflow pressure regulation from 3 to 35 centimeters of water.

The failsafe base line limiting control valve 218 functions with the demand base line compensator 192 to provide a base line deviation control system which has a soft flow. By closing down the base line limiting control valve 218 the base line is increasingly dampened providing a "soft, spongy type flow governing". This causes the exhalation of valve member 241 to increase outflow for any selected base line. Therefore, the demand base line compensator would permit more gas to flow to hold any given base line because of the additional pneumatic clutching at the exhalation valve member 241.

Associated with the additional outflow at any given base line is the ability of the demand base line compensator 192 to respond more rapidly to a drop in base line pressure decreasing downwardly with base line deviation. Therefore, the failsafe base line limiting valve provides means of adjustably regulating base line deviation during physiological spontaneous base line control.

The failsafe base line limiting orifice 218 provides a maximum base line limit should the demand base line compensator 192 fail in service. The maximum governing pressure provided with the orifice 218 receiving an inlet pressure of 50 p.s.i. would be approximately 50 centimeters of water.

Utilization of gas from the socket 207 to provide nebulization of the gas supplied to the patient will not affect the operation of the exhalation valve hereinbefore described.

As can be seen from FIG. 8, overpressure relief valve means 258 has been provided which is in communication with the inlet end of the master venturi assembly 199. It has been found that such an arrangement is particularly satisfactory where it is desired that the overpressure relief valve operates at relatively low pressure as, for example, in neo-natal applications. It has been found that a flapper type of relief valves can be utilized in such applications and that they are more sensitive at lower pressures because they are sensing the pressure which is in excess of that which is created by the jets 198 and 213 passing through the venturi throat 258.

It is apparent from the foregoing that there has been provided a ventilator which is very versatile and has only one control valve. Even though it is relatively simple, it has great capabilities particularly in that it is possible to provide a constant positive airway pressure against which the patient must exhale and which can be readily adjusted. It is also provided with an overpressure relief valve which is particularly adapted to low pressure applications as, for example, with babies.

What is claimed is:

1. In a ventilator having an inhalation phase and an exhalation phase in its operative cycle for use with a source of gas under pressure, a master sequencing cartridge having an inlet adapted to be connected to the source of gas under pressure and an outlet, a valve member movable between open and closed positions for controlling the flow of gas from the inlet to the outlet, diaphragm means for moving said valve member between open and closed positions and forming first and second chambers in the cartridge on opposite sides of the diaphragm means, a breathing circuit outlet, breathing circuit means coupling the breathing circuit outlet to the outlet of the master sequencing cartridge, a demand base line compensator having an inlet connected to the source of gas under pressure and an outlet coupled to the breathing circuit outlet, a valve member movable between open and closed positions for controlling the flow of gas from the inlet to the outlet of the compensator, diaphragm means for moving the valve member of the compensator between open and closed positions and forming first and second chambers on opposite sides of the diaphragm means, means coupling the first chamber of the compensator to the breathing circuit outlet, adjustable means for yieldably biasing said diaphragm means of the compensator towards a closed position, a single volume/rate control valve assembly having an inlet and an outlet with an orifice interconnecting the same and an ajustable needle valve disposed in the orifice, means coupling the inlet of the control valve assembly to the outlet of the master sequencing cartridge, means connecting the outlet of the control valve assembly to the first chamber on one side of the diaphragm means to bleed gas through the control valve assembly in one direction into said first chamber to move said valve member to terminate the inspiratory phase and initiate the expiratory phase and thereafter to bleed off gas from the first chamber through the control valve assembly into the breathing circuit means whereby after sufficient bleed-off of gas from the first chamber the valve member moves to the open position to terminate the expiratory phase and initiate the inspiratory phase, said volume/rate control valve assembly serving as a single adjustable control for the ventilator to control both the length of the inspiratory phase and the length of the expiratory phase.

2. A ventilator as in claim 1 together with a balance reservoir connected between the outlet of the volume/rate control valve assembly and said first chamber of said master sequencing cartridge and a balance orifice connected between said additional flow path means and the inlet of said control valve assembly.

3. A ventilator as in claim 1 wherein the breathing circuit means includes a venturi assembly connected to the breathing circuit outlet together with an emergency intake valve assembly coupled to the proximal end of the venturi assembly.

4. A ventilator as in claim 1 wherein said means coupling the breathing circuit outlet to the outlet of the master sequencing cartridge includes an inspiratory flow/volume control valve assembly having an adjustable orifice therein.

5. A ventilator as in claim 1 wherein said master sequencing cartridge includes a sealing member for separating said valve member from said diaphragm, said sealing member being exposed to gas under pressure from the source of gas when the valve member has been moved to an open position so that the piston effect keeping the valve member in an open position is greater after the valve member has been opened than prior to the opening whereby there is a large differential between opening pressure of the valve member and the pressure required to close the valve member.

6. In a method for controlling the inhalation phase and the exhalation phase in the operative cycle of a ventilator supplied with gas from a source of gas under pressure by the use of a single adjustable volume/rate control valve assembly in conjunction with a master sequencing cartridge having a diaphragm operated valve member for controlling the flow of gas to the patient with a normally open position and a chamber on one side of the diaphragm for receiving gas to move the diaphragm operated valve member to a closed position, initiating the flow of gas from the source of gas to the master sequencing cartridge bleeding gas from the source of gas at a controlled rate through the single volume/rate control valve assembly in one direction into the chamber to move the valve member to a closed position to terminate inspiratory flow, bleeding gas from the chamber at a controlled rate through the single volume/rate control valve assembly in an opposite direction to terminate the expiratory flow, using the differential in opening and closing pressures for the diaphragm operated valve member to obtain a ratio between inspiratory and expiratory times and bleeding off additional gas from the chamber through a passage independent of the single volume/rate control valve assembly to adjust the ratio of the length of the inspiratory phase to the length of the expiratory phase.

7. In a ventilator having an inhalation phase and an exhalation phase in its operative cycle for use with a source of gas under pressure, a master sequencing cartridge having an inlet adapted to be connected to the source of gas under pressure and an outlet, a valve member movable between open and closed positions for controlling the flow of gas from the inlet to the outlet, diaphragm means for moving said valve member between open and closed positions and forming first and second chambers in the cartridge on opposite sides of the diaphragm means, a breathing circuit outlet, breathing circuit means coupling the breathing circuit outlet to the outlet of the master sequencing cartridge, a demand base line compensator having an inlet connected to the source of gas under pressure and an outlet coupled to the breathing circuit outlet, a valve member movable between open and closed positions for controlling the flow of gas from the inlet to the outlet of the compensator, diaphragm means for moving the valve member of the compensator between open and closed positions and forming first and second chambers on opposite sides of the diaphragm means, means coupling the first chamber of the compensator to the breathing circuit outlet, adjustable means for yieldably biasing said diaphragm means of the compensator towards a closed position, a volume/rate control valve assembly having an inlet and an outlet, means coupling the inlet of the control valve assembly to the outlet of the master sequencing cartridge, means connecting the outlet of the control valve assembly to the first chamber on one side of the diaphragm means to bleed gas through the control valve assembly in one direction into the first chamber to move said valve member to terminate the inspiratory phase and initiate the expiratory phase and thereafter to bleed off gas from the first chamber through the control valve assembly in an opposite direction into the breathing circuit outlet whereby after sufficient bleed-off of gas from the first chamber the valve member moves to the open position to terminate the expiratory phase and intiate the inspiratory phase, said volume/rate control valve assembly serving as a single control for the ventilator to control both the length of the inspiratory phase and the length of the expiratory phase and an additional flow path means coupled between said first chamber and said breathing circuit means for bleeding off gas from said first chamber to said breathing circuit outlet and including a one-way check valve for only permitting flow of gas from said first chamber and an adjustable control valve in series with said one-way check valve for controlling the rate of flow of gas from said first chamber to thereby make possible adjustment of the ratio of the length of the inspiratory phase to the length of the expiratory phase.

* * * * *